(12) United States Patent
Holmquist et al.

(10) Patent No.: US 7,440,805 B2
(45) Date of Patent: Oct. 21, 2008

(54) IMPLANTABLE PULSE GENERATOR SYSTEM AND METHOD FOR UTILIZING COMMUNICATION PROTOCOLS

(75) Inventors: Paul J. Holmquist, Andover, MN (US); Al Koshiol, Lino Lakes, MN (US); Joe Bange, Eagan, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 167 days.

(21) Appl. No.: 10/630,454

(22) Filed: Jul. 30, 2003

(65) Prior Publication Data

US 2005/0027329 A1 Feb. 3, 2005

(51) Int. Cl.
*A61N 1/00* (2006.01)
(52) U.S. Cl. ........................................ 607/32
(58) Field of Classification Search ................ 607/60, 607/59, 30, 32; 600/300
See application file for complete search history.

(56) References Cited

U.S. PATENT DOCUMENTS

| | | | | |
|---|---|---|---|---|
| 5,720,770 | A * | 2/1998 | Nappholz et al. | 607/30 |
| 6,083,248 | A * | 7/2000 | Thompson | 607/30 |
| 6,250,309 | B1 | 6/2001 | Krichen et al. | 128/899 |
| 6,442,434 | B1 | 8/2002 | Lee | 607/59 |
| 6,497,655 | B1 * | 12/2002 | Linberg et al. | 600/300 |
| 6,577,899 | B2 * | 6/2003 | Lebel et al. | 607/60 |
| 6,662,052 | B1 * | 12/2003 | Sarwal et al. | 607/59 |
| 6,699,187 | B2 * | 3/2004 | Webb et al. | 600/300 |
| 6,871,211 | B2 * | 3/2005 | Labounty et al. | 709/203 |
| 6,985,762 | B2 * | 1/2006 | Brashears et al. | 600/323 |
| 2001/0023360 | A1 * | 9/2001 | Nelson et al. | 607/60 |
| 2001/0031997 | A1 * | 10/2001 | Lee | 607/59 |
| 2002/0023654 | A1 * | 2/2002 | Webb | 128/899 |
| 2002/0045804 | A1 * | 4/2002 | Christopherson et al. | 600/300 |
| 2002/0049480 | A1 * | 4/2002 | Lebel et al. | 607/60 |

OTHER PUBLICATIONS

Kostas Pentikousis, TCP in Wired-Cum-Wireless Environments, IEEE Communications Surveys, Fourth Quarter 2000 pp. 1-14.

* cited by examiner

*Primary Examiner*—George Manuel
*Assistant Examiner*—Christopher A. Flory
(74) *Attorney, Agent, or Firm*—Schwegman, Lundberg & Woessner, P.A.

(57) ABSTRACT

An implantable pulse generator communicates with external devices such as device programmers and network repeaters to exchange data. The communication utilizes a communication protocol such that data is transferred in packets and transport control information is included for each of the packets. Network routing information may also be provided for each of the packets to establish additional capabilities including network addressing, priority control, or recipient validation. Information exchange instructions are executed by the implantable pulse generator to take data from one or more application programs being executed by the implantable pulse generator, divide the data into packets, and add the transport control information, and network routing information if desired, for outgoing packets. Additionally, the information exchange instructions may be executed by the implantable pulse generator to extract the network routing information if available and the transport control information from incoming packets and to reconstruct the data from the packets and provide the data to the one or more application programs.

40 Claims, 6 Drawing Sheets

IMPLANTABLE PULSE GENERATOR SYSTEM AND METHOD FOR UTILIZING COMMUNICATION PROTOCOLS

TECHNICAL FIELD

The present invention relates to establishing communication between an implantable pulse generator and an external device. More specifically, the present invention relates to utilizing a communication protocol in conjunction with a separate application program of an implantable pulse generator to transfer data between the implantable pulse generator and the external device.

BACKGROUND

Implantable pulse generators such as pacemakers and defibrillators provide cardiovascular therapy to patients. Electrical stimulation such as electrical pulses or electrical shocks is provided to the patient's heart by the implantable pulse generator to control the heart's function, such as controlling the rhythm and/or pace. The implantable pulse generators generally employ application programs that control various behaviors of the implantable pulse generators. For example, an application program may be executed by a processing device to perform a particular therapy routine and/or to provide monitoring and data gathering of the patient's cardiovascular condition. An application program may also be executed to allow the implantable pulse generator to communicate externally, either to send or receive data with a device programmer or other external device.

Conventionally, the implantable pulse generator communicates under the control of an application program. The external device in communication with the implantable pulse generator utilizes a complimentary application program so that there is a compatible exchange of data between the two devices. Thus, a standardized communication protocol is not utilized since the communication is directly between the application programs of the two devices. However, because there is no standardized form of communication, the implantable pulse generator is limited in its ability to communicate with a variety of devices and application programs.

Furthermore, the exchange of data typically occurs over an inductive coupling established by the close proximity of a magnetic wand to the implantable pulse generator. Therefore, the addressing of the data is not required since the broadcasted data can only be received by the wand placed at the implantable pulse generator. However, it remains desirable to have an implantable pulse generator that can communicate over an inductive link without requiring each application program to establish the communication protocol. Additionally, for implantable pulse generators that have longer range capabilities through radio frequency communication and/or through downstream network transmissions, data being transmitted without addressing information may not be delivered to an intended recipient and/or may be delivered to an unintended recipient.

SUMMARY

Embodiments of the present invention address these and other problems by exchanging data through data packets. The data packets are provided with header information through use of a set of information exchange instructions. These instructions are application independent so that different applications may utilize the instructions to send and receive data. These instructions provide transport control information so that the data may be properly reconstructed from the data packets being exchanged and may also provide network routing information for the data packets being exchanged between devices so that the data packets are directed to the correct recipient device and/or are delivered with the appropriate priority.

One embodiment is a method of exchanging data with an implantable pulse generator device for providing cardiovascular therapy to a patient. The method involves executing at the implantable pulse generator device at least one application program that provides data that is to be exchanged. The method also involves executing at the implantable pulse generator device a set of information exchange instructions on the data obtained from the application program. The information exchange instructions are executed to divide the data into packets and apply header data to each packet. The header data provides transport control information that indicates how to reconstruct the data from the data packets. The method also involves wirelessly transmitting from the implantable pulse generator device each of the packets having the header data.

Another embodiment is an implantable pulse generator device for providing cardiovascular therapy to a patient. The implantable pulse generator includes at least one processing device configured to execute at least one application program to control the generation of electrical stimulation to provide the cardiovascular therapy. The at least one application program is also executed to utilize received data. The at least one processing device is further configured to execute a set of information exchange instructions to obtain incoming data packets. Header data that provides transport control information is extracted from each of the incoming data packets to allow the data to be reconstructed from the packets for use by the at least one application program. A pulse generator in communication with the at least one processing device is included to generate electrical stimulation to provide the cardiovascular therapy. A receiver in communication with the at least one processing device is included to receive the incoming data packets having the transport control information and provide the incoming data packets to the at least one processing device.

Another embodiment is a method of transferring data between a data network and an implantable pulse generator utilizing transport layer connections to transfer data in packets wherein the data network has a wired connection to a repeater in proximity to the implantable pulse generator and wherein the repeater has a wireless connection to the repeater. A first transport layer connection is established between the data network and the repeater over the wired connection. A second transport layer connection is established between the repeater and the implantable pulse generator over the wireless connection. A first data packet with first transport control header information is transferred from the data network to the repeater over the first transport layer connection. The first data packet with second transport control header information is transferred from the repeater to the implantable pulse generator over the second transport layer connection.

Another embodiment is a system for transferring health care data that includes a data network and an implantable pulse generator. The system also includes a repeater located in proximity to the implantable pulse generator. The repeater has a wired connection to the data network and a wireless connection to the implantable pulse generator. A first transport layer connection is established between the repeater and the data network and a second transport layer connection is established between the repeater and the implantable pulse generator. Data packets traverse both the first transport layer connection and the second transport layer connection when passing between the data network and the implantable pulse generator.

DETAILED DESCRIPTION

Embodiments of the present invention provide implantable pulse generators such as pacemakers and defibrillators that implement communications protocols to exchange data with external devices. The communications protocols relieve the application programs of the implantable pulse generator from establishing the communication protocol with the low levels of the communication stack such that the communications protocols may be implemented for a diverse set of application programs. Furthermore, the communications protocols provide functionality including disassembly of data into packets for transmission and reassembly of packets to data for use by application programs. The communications protocols may also provide additional functionality including the routing of data packets by including network address information.

Figure 1:
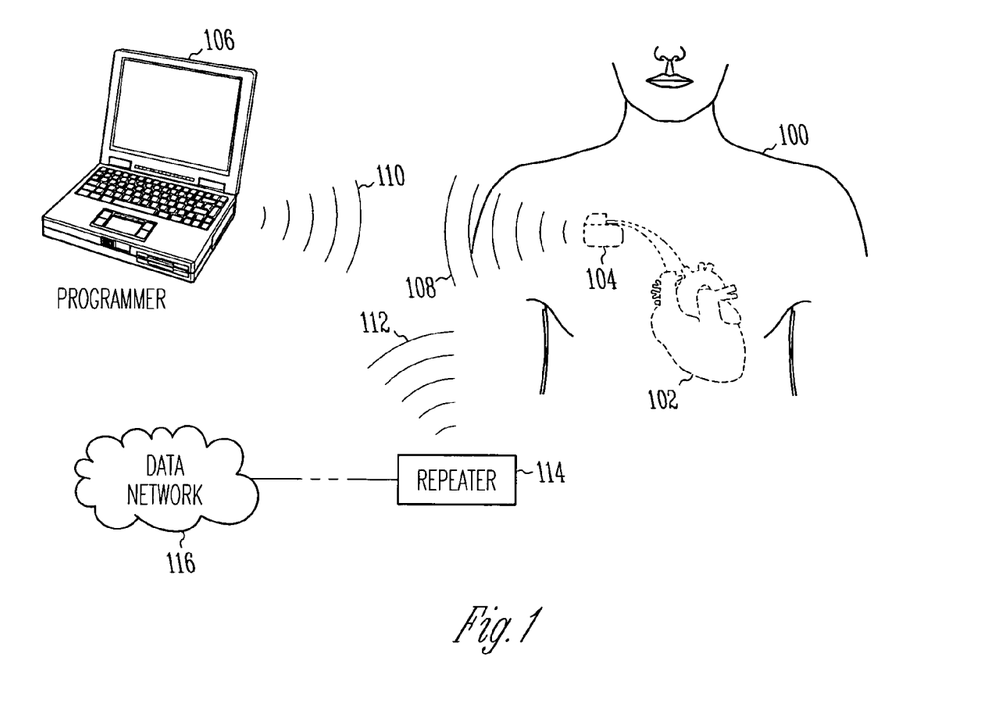
FIG. 1 illustrates a typical communication environment for an implantable pulse generator device according to an embodiment of the present invention.

A typical operating environment for systems according to the present invention is shown in FIG. 1. A patient 100 has an implantable pulse generator 104 that provides therapy and/or monitoring for the heart 102 of the patient 100. The implantable pulse generator 104 transmits wireless signals 108 containing data packets typically subdivided into data frames to external devices to transfer data to the external devices for review, such as trending data or real-time electrogram data. The wireless signals 108 may be magnetic signals that are exchanged via inductive coupling between the implantable pulse generator 104 and an external device. Alternatively, the wireless signals 108 may be radio frequency electromagnetic signals that are exchanged between an RF transceiver of the implantable pulse generator 104 and an external device.

External devices receive the signal 108 through the inductive coupling or RF transmission. The external devices receiving the signal 108 may be of various forms such as a device programmer 106. The device programmer 106 performs analysis on the data or displays the data for review by a physician. The device programmer 106 may also generate wireless signals 110 having data packets subdivided into data frames that are transferred to the implantable pulse generator 104 through RF or an inductive coupling. The device programmer 106 may send real-time control information, device therapy programming, or other information to the implantable pulse generator 104.

Another form of external device that may receive the signal 108 from the implantable pulse generator 104 is a repeater 114. The repeater 114 transfers the information received in the signal 108 to a downstream data network 116 typically through a wired network connection. The data network 116 may be a dedicated wide area network ("WAN") or a public data network such as the Internet. Other connections to downstream devices are possible as well, including dial-up connections through a public telephone network or other public infrastructure. The repeater 114 may perform basic router functions to forward data packets to downstream network devices as instructed by the network routing information included in data packets of the signal 108. The repeater 114 may also deliver data packets subdivided into data frames from the data network 116 that are addressed to the implantable pulse generator 104 through wireless signal 112, which may be through RF or inductive coupling. Thus, the repeater 114 allows remote management of the implantable pulse generator 104 by linking the implantable pulse generator 104 to a downstream monitoring device through the data network 116.

Figure 2:
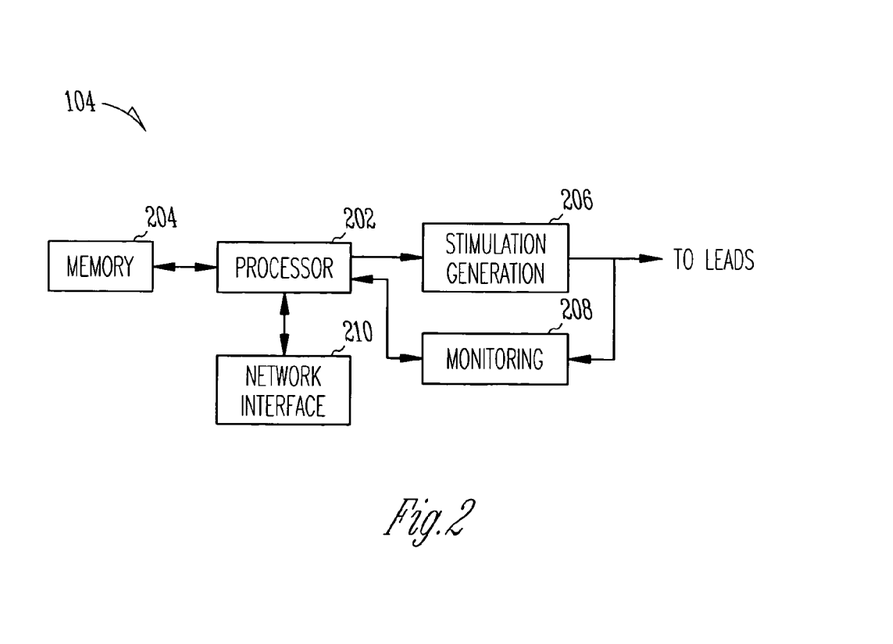
FIG. 2 shows components of an embodiment of an implantable pulse generator device in accordance with the present invention.

FIG. 2 illustrates the components of an implantable pulse generator 104. The implantable pulse generator 104 includes one or more processing devices 202 that perform various processing functions. The processing device 202 typically executes some form of operating system providing basic services to exchange data with memory 204 when executing application programs to provide therapy, monitoring, and/or communication functions.

Through execution of application programs, the processor 202 controls an electrical stimulation module 206 that has circuitry to provide electrical stimulation in the form of pulses and/or shocks to the heart 102 of the patient 100 through electrical leads extending to the various regions of the heart 102. The processor 202 may also control a monitoring module 208 that has circuitry to detect electrical activity of the heart 102 through the leads and provide data indicative of the electrical activity to the processor 202 where it can be stored, analyzed, and/or used to control the electrical stimulation module 206.

Also through execution of application programs, the processor 202 sends and receives data for exchange with external devices. The processor 202 communicates with a network interface 210 to exchange data packets. The network interface 210 establishes communication with the external device through an inductive or RF wireless link to exchange the data packets.

The processor 202 generates the data packets from data of the application program by implementing information exchange instructions to divide application data into packets and provide header data for each packet. Likewise, the processor 202 implements the information exchange instructions to extract and analyze the header data and to reconstruct application data from the data packets accordingly. The header data may be contained in one or more layered headers applied to the data packets. For example, one header layer may provide transport control information that instructs the processor 202 as to how the application data may be reconstructed from the data packets. The transport control information of the header layer may provide additional instruction for the processor 202 as well as discussed below with reference to FIG. 3. Another header layer may be included outside of the transport control header to provide network routing information, such as the network address of the intended recipient device and/or additional instruction as discussed below with reference to FIG. 3.

The memory 204 of the implantable pulse generator 104 includes random access and read only memory to store the operating system and application program code being executed by the processor 202 as well as data received from monitoring module 208 that may later be transferred to an external device for review. Additionally, the memory 204 stores the information exchange instructions that are implemented by the processor 202 to handle the data packets and the transport control and network routing header data. The memory 204 provides a buffer space to allow the processor 202 to generate and buffer outgoing data packets as well as buffer and reconstruct application data from incoming data packets.

Figure 3:
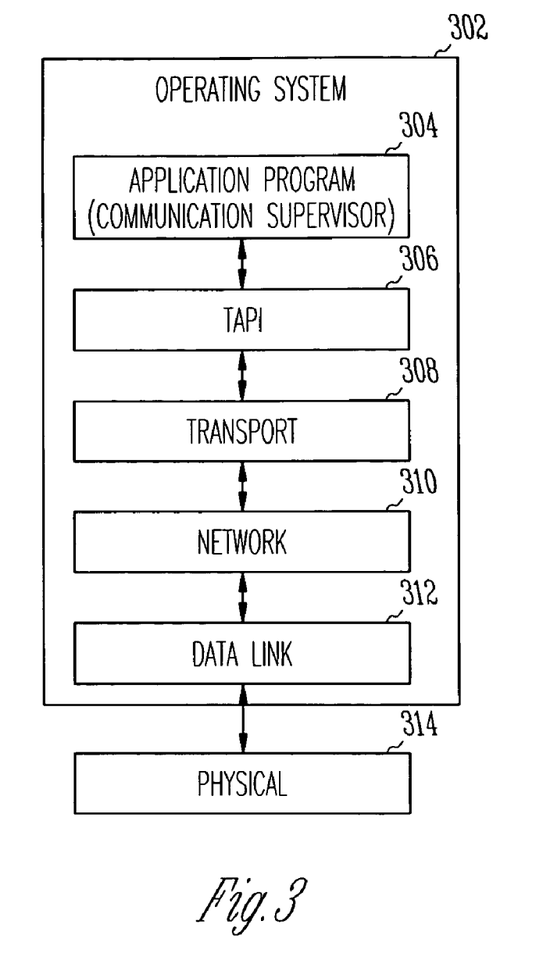
FIG. 3 illustrates a communications stack as implemented by the implantable pulse generator of FIG. 2.

FIG. 3 illustrates a communication stack implemented by the implantable pulse generator 104 according to an embodiment of the present invention. An operating system 302 is executed by the processor 202 from memory 204 to provide a platform upon which the subsequent layers of the communication stack may be performed and provides basic services that layers of the stack utilize to function and to interface to the other layers. Such basic services include access to buffer space and code in memory 204 and access to the physical layer aspects of the network interface 210. The operating system 302 provides additional basic services as well such as timer services and event notifications.

The application program layer 304 resides atop the stack. In this embodiment, the application program layer 304 provides a communication supervisor that receives incoming data for the application program from lower levels of the stack. For example, incoming data may be a command to an application program to begin streaming data received from the monitoring module 208, such as electrogram data. The communication supervisor also controls the sending of data to external devices, such as streaming the electrogram data. The communications supervisor of the application program 304 may send and receive data through a standard interface to the lower levels of the communication stack, such as a telemetry application programming interface ("TAPI").

The TAPI layer 306 of this embodiment interfaces the communications supervisor of the application program 304 to the transport layer 308. The TAPI layer 306 provides the services needed by the communications supervisor for messaging and control of the lower layers of the stack. Examples of the TAPI services include standard socket management that translates and maps communication supervisor requirements into functional interfaces/services. These services include establishment/termination notifications, interfaces for sending and receiving application data and flow-control of that data. The TAPI services also configure and set up the lower layers including the transport and network layers based on functional requirements, which occurs per patient communication session.

The transport layer 308 is implemented by information exchange instructions that are executed by the processor 202. The transport layer 308 may provide a standard transport layer protocol such as the transmission control protocol ("TCP"), the TCP for transactions protocol ("T/TCP"), the User Datagram Protocol ("UDP") or other known transport layer protocols that provide either streaming or record based exchange of application data. Other transport control protocols that may be utilized include ATM Adaptation Layer protocol and Service Specific Connection Oriented Protocol. Transport control information is included in a header for each outgoing packet to instruct a processor of an external device implementing the same transport protocol as to how the packets are used to reconstruct the application data. Similarly, transport control information is included in a header for each incoming packet to instruct the processor 202 implementing transport layer 308 as to how the incoming packets should be used to reconstruct application data.

Such transport control information may provide one or more various pieces of information that is used to reconstruct application data from the packets. For example, protocol version information may be specified where multiple protocols may be in use. Packet sequence information may be specified where protocols are used that allow packets to be communicated out of sequence. Packet integrity may be checked by some transport protocols by performing checksums or CRC algorithms to the data so that if a packet is not acceptable a request for resending of the packet can be returned or an acknowledge is not sent. Socket information implied by the transport and network layers specifies the socket that a particular packet corresponds to where multiple sockets are established between devices. Other pieces of information that may be included in the transport control information header include source/destination port numbers, the checksum value and length of the payload as well as flow-control information such as window size, sequence and acknowledgement information based on the type of transport utilized for a socket.

The transport protocol to be used may be dependent upon the type of data being transferred, which determines how reliable or fast the data transfer should be. Where reliable connections are required, more elaborate transport protocols may be used such as TCP where socket connections with error checking and security are employed. Where high throughput is required, less elaborate transport protocols may be used such as UDP which does not perform handshaking and error checking.

In certain embodiments of the implantable pulse generator 104, various transport protocols may be selectable for use with outgoing data by the communication supervisor of the application program layer 304. Thus, if the application program 304 requires fast throughput, such as for real time data, the communications supervisor may instruct the TAPI layer 306 to choose the UDP transport protocol of transport layer 308. If the application program 304 requires a highly reliable connection, such as for transfer of therapy routines, the communications supervisor may instruct the TAPI layer 306 to choose the TCP transport protocol.

In the network layer 310, information exchange instructions enacting this layer cause the processor 202 to add network routing header information to the outgoing packets containing the transfer control header information previously added by the transport layer 308. Likewise, the network layer 310 extracts the network routing header information from incoming packets prior to passing the incoming data packets to the transport layer 308. Several varieties of network routing information may be utilized, including the fourth version of IP ("IPv4"), the sixth version of IP ("IPv6"), or other known protocols for the network layer 310. Other examples of network layer protocols that may be used include IPX, AppleTalk, System Network Architecture, DECnet, or CLNP.

The network routing information includes a network address of the intended recipient that allows a data packet to be properly forwarded and/or used as a final destination verification at the intended recipient device. The network routing information also includes a network address of the sender that allows the recipient to return an outbound response, such as an acknowledgement of an inbound packet or data requested by the inbound message. Additional information may also be include in the network routing information header such as the protocol version where multiple protocols are in use as well as packet prioritization, discussed below, where packets are not necessarily sent or forwarded in the order queued or received. Other pieces of information that may be included in the network routing information header include fragmentation/reassembly, time-to-live, timestamp, and routing path information.

Packet prioritization information may be included in the network layer header for packets being exchanged with the implantable medical device. One example of providing packet prioritization for IP headers involves utilizing the Type-of-Service ("TOS") field of the IP header. While parts of the TOS field are used for various purposes including packet handling requests, see network RFC 1349, the precedence field within the TOS field is not used for sending packets to a host endpoint. Thus, the application may utilize a common socket API (e.g., setsockopt) to define the priority within the 3 bits of the precedence field. The data link/physical layer may then refer to the precedence field when determining the priority of packets to send. Those frames of a packet with higher priority are sent by the data link layer prior to the frames of packets with lesser priority. This prevents large, low priority packets from delaying the transmission of high priority packets such that the data link layer may begin sending frames of a higher priority packet before completing transmission of all frames for a lower priority packet.

In addition to the previous programming interfaces that utilize the transport and network layers to establish communications between the pulse generator and external devices, an X/Open Transport Interface ("XTI") may be employed by the pulse generator. XTI is the programming interface to the service provided by these transport and network layers.

Upon completing the addition of the transport header data and the network header data if required, each data packet is distributed to the data link layer 312 for transmission. The data link layer 312 involves interaction between the processor 202 executing data link code from memory 204 and the network interface 210 in communication with the physical link. The data link layer 312 provides the conventional data link operations of packaging the data for transmission over the physical link such as dividing packets into frames. The data link layer 312 utilizes medium access control of the network interface 210 to compete for access to the physical link. Upon winning access to the physical link, the physical layer 314 whose functions are provided by the network interface 210 moves the raw bits of data wirelessly to or receives the raw bits of data wirelessly from the external device.

Various optimizations may be utilized to improve the performance of the transport layer 308 and/or network layer 310 for application with the implantable pulse generator 104. Thread execution time may be reduced by optimizing checksums when used and by avoiding or splitting copy operations. Additional optimization may be attained by either utilizing T/TCP or persistent TCP socket connections that persist throughout a patient telemetry session. All unutilized services of a particular transport or network protocol may be removed leaving the minimal services necessary to be a valid network host. For example, segmentation through IP may be removed where sufficient segmentation is provided by the transport layer 308 and/or data link layer 312. Other unutilized services that can be removed include address resolution of the IP protocol, UDP checksums, selective acknowledgements from the TCP protocol, Routing Information Protocol services, Internet Group Management Protocol services, and the Simple Network Management Protocol services.

Figure 4:
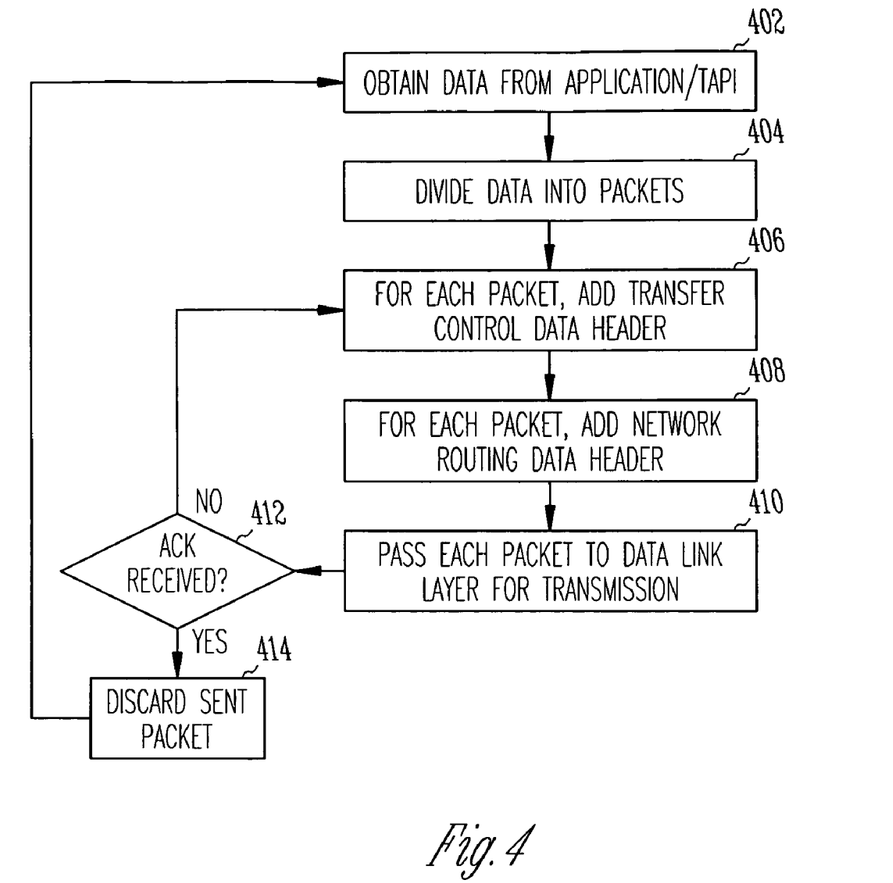
FIG. 4 shows the operational flow of the transport and network layers of the stack of FIG. 3 for outgoing data.

FIG. 4 illustrates the basic logical operations performed by the information exchange instructions being executed by the processor 202 to handle the transport layer 308 functions, and network layer 310 functions where necessary, for outgoing data packets. Initially, the application data to send is obtained at the transport layer 308 from the application program 304 through a standard interface such as TAPI 306 at data operation 402. Upon obtaining the data, the transport layer 308 divides the data into packets for transmission at packet operation 404.

For each packet that is produced at packet operation 404, header data is then added. Initially, the transport layer 308 adds transport control header information for each packet at transport operation 406. The packet having the transport control header information is passed to the network layer 310 where network routing header information is added at network operation 408. Then the packet containing the transport control and network routing information is passed to the data link layer for transmission at data link operation 410.

Upon sending a packet, the transport layer begins to determine whether an acknowledgement message has been received from the intended recipient of the sent packet at query operation 412. Such an acknowledgement message is received via the logical operations 502-510 of FIG. 5 for receiving packets, discussed below. If the transport layer does not detect that an acknowledgement has been received, then operational flow returns to packet operation 404 where the packet is passed down the layers to receive the transport, network, and data link header information and is sent again to the recipient. Typically, this re-send occurs after a timeout period maintained by the transport layer. If query operation 412 detects that an acknowledge message has been received, then the packet that has been sent is discarded at packet operation 414. Operational flow then returns to data operation 402.

Figure 5:
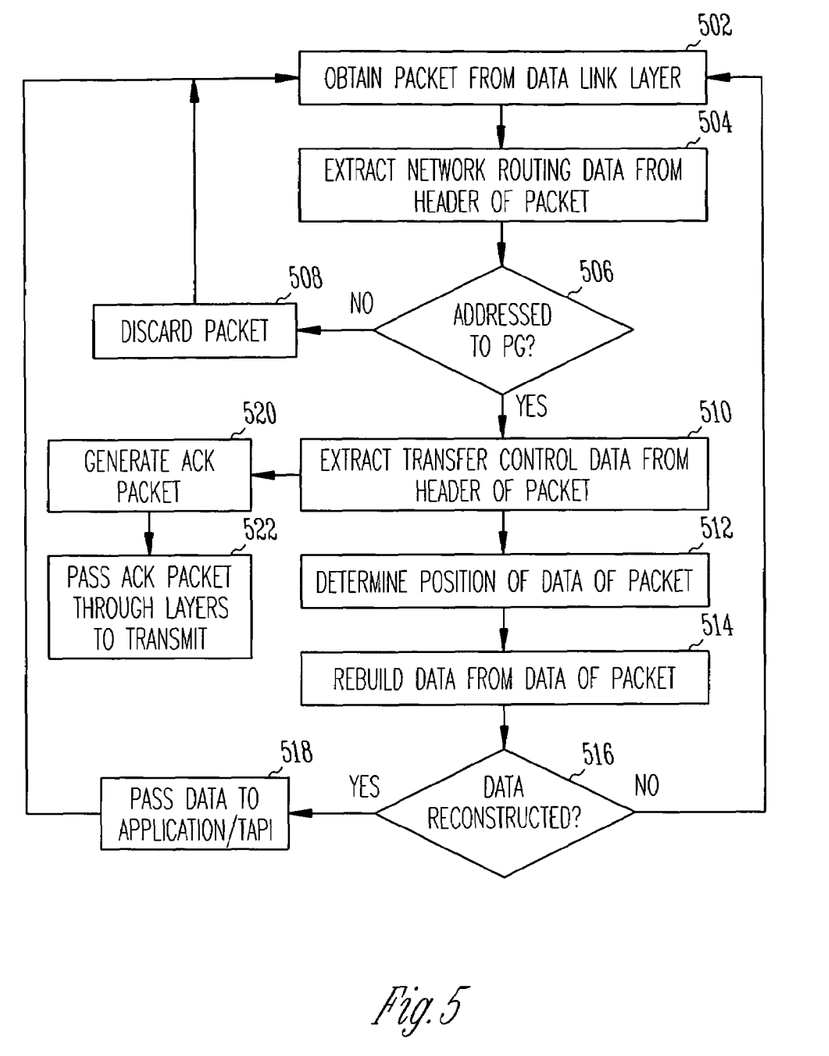
FIG. 5 shows the operational flow of the network and transport layers of the stack of FIG. 3 for incoming data.

FIG. 5 illustrates the complementary basic logical operations performed by the information exchange instructions being executed by the processor 202 to handle the transport layer 308, and network layer 310 functions where necessary, for incoming data packets. Initially, the received data packets are obtained from the data link layer at data link operation 502. Then, the network routing information is extracted from the header of each packet at network operation 504. Upon extracting the information, the network layer 310 may simply discard this information and proceed to transport operation 510 or may perform an additional verification that the packet was intended for the implantable pulse generator 104 at query operation 506. If query operation 506 detects that the network address contained in the network routing information does not match the network address of the implantable pulse generator 104, then the packet is discarded at packet operation 508. If the network address matches, then operational flow proceeds to transport operation 510.

At transport operation 510, the transport layer 308 extracts the transport control information from the remaining header of the packet. From the transport control information previously extracted, the transport layer 308 then determines the position of the data from the packet for the application data being reconstructed at position operation 512. Determining the position of the data from the packet may involve determining the socket that the packet corresponds to where the socket is associated with a particular piece of application data being reassembled. Furthermore, determining the position of the data from the packet may involve determining the proper sequence of this piece of data in relation to pieces of data sent in other packets where the sequence is not necessarily the same as the sequence in which the packets are received.

As the information exchange instructions for transport layer 308 continue to reassemble the application data from the received data packets, query operation 516 continues to detect from the packet sequence whether the application data has been completely reconstructed. When it is detected that the application data is incomplete, operational flow returns to packet operation 502 where additional packets are obtained from the data link layer 312. Upon detecting that the application data has been reconstructed at query operation 516, the information exchange instructions of transport layer 308 pass the data up to the application program 304 where further reconstruction may occur if necessary through the intermediate TAPI interface 306, at data operation 518.

Returning to transport operation 510, once the transport layer has extracted the transfer control data from the packet, in addition to operational flow transitioning to position operation 512, operational flow branches to packet operation 520 where an acknowledge packet is generated. Once generated, this packet is sent down the layers and transmitted back to the sender of the received packet at acknowledge operation 522 via operations 406-410 of FIG. 4 for sending packets as discussed above. As also discussed above, the transport layer of a sender checks for receipt of this acknowledge packet, such as at query operation 412 of FIG. 4, to determine whether to re-send the data packet to the recipient.

Figure 6:
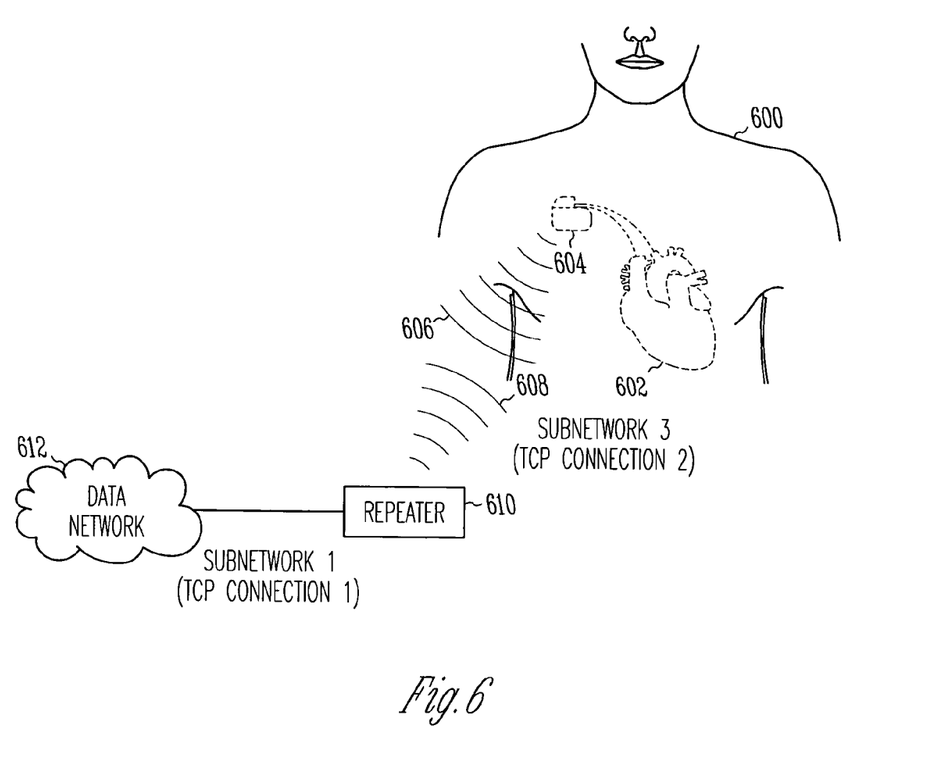
FIG. 6 shows an alternative configuration to the communication system environment for an embodiment of the present invention.

FIG. 6 illustrates an alternative system of transferring information between an implantable pulse generator 604 and a data network 612. As with FIG. 1, the pulse generator of patient 600 is linked to the patient's heart 602 and transmits wireless signals 606. Furthermore, a repeater 610 receives the signals 606 and transmits wireless signals 608 back to the pulse generator 604. The repeater 610 has a wired connection to a data network 612.

The system of FIG. 6 addresses issues caused by utilizing certain standard transport protocols such as TCP when transmitting data over a wireless link between a data network and a pulse generator, such as through a repeater. While the lower layers of the stack may deal with re-tries of communication without causing a breakdown in the communication system, the transport layer of the pulse generator 604 or data network 612 may see the delay as indicating lost packets and then begin to increase the retransmission of packets exponentially up to a predefined maximum value. There is a re-transmission timeout for each time a packet is retransmitted, and this timeout also increases exponentially. After several consecutive re-transmission timeouts for sending packets, the transport layer may consider the link broken such that the sending side drops the connection entirely. Furthermore, because the transport layer does not reset the re-transmission timeout value upon a link being re-established, this value can grow to a large value that causes lengthy delays before a packet can be re-sent even though the link to send over may be available during the lengthy delay.

As shown in FIG. 6, this system addresses these issues by providing two transport layer connections, one for each subnetwork that is present. The first transport layer connection is established between the pulse generator 604 and the repeater 610 for the wireless subnetwork. Additionally, the second transport layer connection is established between the repeater 610 and the data network 612 for the wired subnetwork. Because the repeater 610 acts as the bridge between the two subnetworks, the repeater 610 must perform bridging operations, discussed below with reference to FIG. 7, between the two transport layer connections rather than perform simple router functions like the repeater 114 of FIG. 1.

Thus, the repeater 610 maintains separate transport layer connections to avoid the issues above. The transport layer connection between the repeater 610 and the data network 612 is a reliable wired connection so that neither device experiences enough re-transmission to drop the connection nor establish a lengthy re-transmission timeout. However, this transport layer connection continues to use and benefit from the re-transmission timeout as well as other timeouts of a transport protocol such as TCP. The transport layer connection between the repeater 610 and the pulse generator 604 utilizes a transport layer protocol such as TCP but with this transport layer protocol configured to handle re-transmission timeouts differently. For example, the re-transmission timeout may be set to a relatively small maximum so that there are not significant delays once it reaches its maximum. Alternatively or in addition to this configuration to the transport layer connection, the re-transmission timer and other timers of the transport layer protocol may be reset each time the link is lost so that the maximum re-transmission timeout does not continue upon the link being re-established.

Figure 7:
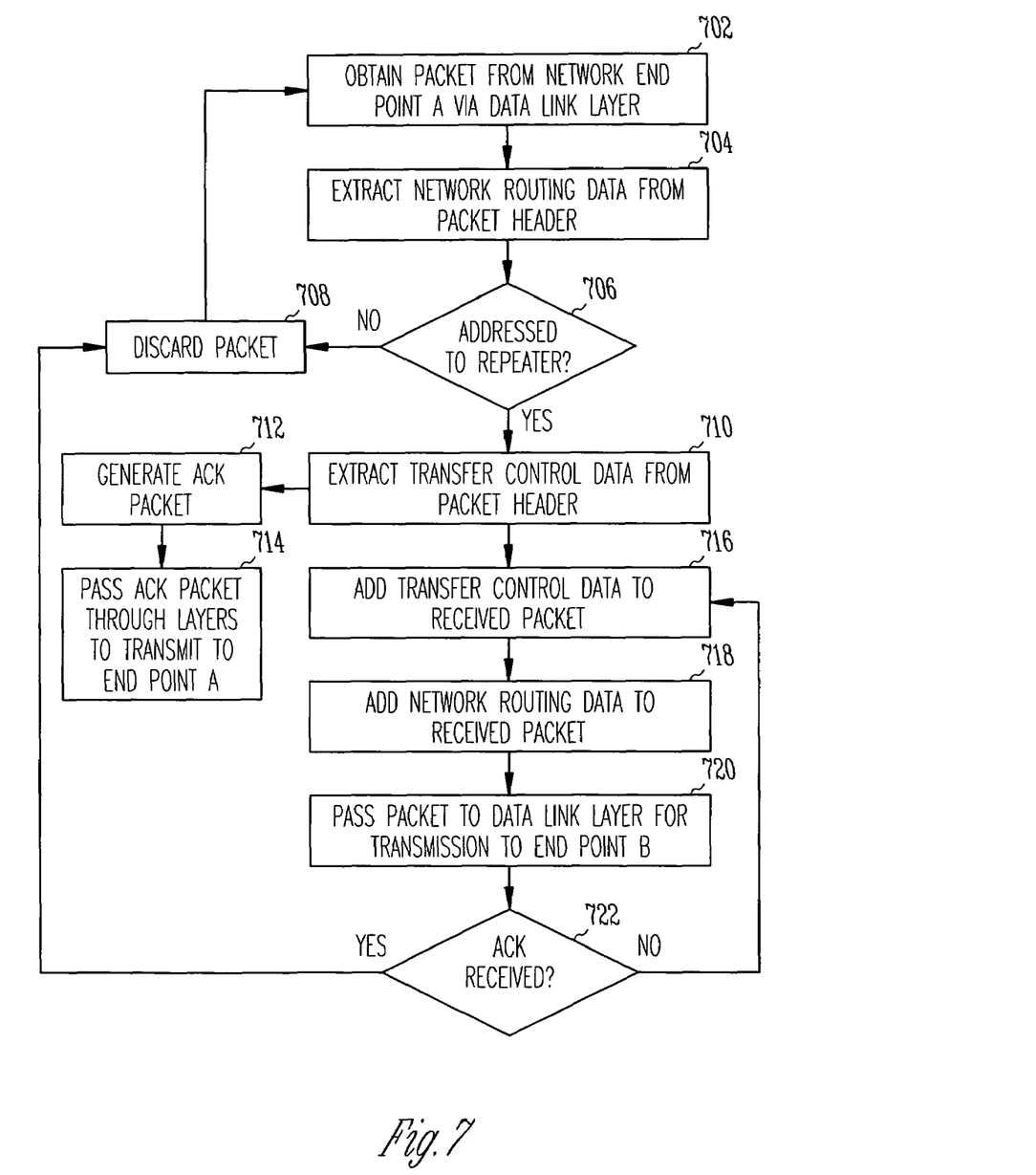
FIG. 7 shows the operational flow of the network and transport layers of the stack of FIG. 3 for the repeater of FIG. 6 when providing communications between the data network and the implantable pulse generator.

FIG. 7 illustrates the bridging operations of the repeater 610. The repeater includes standard components for implementing the communication stack of FIG. 3, including a processor, memory, and network interface. The bridging operations begin by the repeater 610 receiving a packet from a network endpoint A (either the data network 612 or pulse generator 604) over a subnetwork via the data link layer at data link operation 702. Then, the repeater 610 extracts the network routing data from the packet header at network operation 704. The network layer then detects whether the packet is addressed to the repeater 610 at query operation 706.

If the packet is addressed to the repeater 610, then the packet is discarded at packet operation 708. If the packet is addressed to the repeater 610, then the transport layer extracts the transfer control data from the packet header at transport operation 710. The repeater 610 then adds transfer control data for the next subnetwork at transport operation 716. The repeater 610 then adds the network routing data to the packet header for the next subnetwork at network operation 718. The packet is then passed to the data link layer for transmission to endpoint B over this other subnetwork at data link operation 720.

Upon sending the packet over this other subnetwork to endpoint B, the transport layer for repeater 610 begins to detect whether an acknowledgement message has been received at query operation 722 via the operations 702-710. If the acknowledgement message has not been received, then operational flow returns to transport operation 716 where the packet again moves back down the transport and network layers to the data link layer for re-transmission to endpoint B. However, if the acknowledgement message is received, then the transport layer discards that packet at packet operation 708 and operational flow returns to data link operation 702 where another packet is obtained.

Returning to transport operation 716, once the transport layer has extracted the transfer control data from the packet, in addition to operational flow transitioning to transport operation 716, operational flow branches to packet operation 712 where an acknowledge packet is generated. Once generated, this packet is sent down the layers and transmitted back to the sender of the received packet at acknowledge operation 714 via the operations 716-720. As discussed above, the transport layer of a sender checks for receipt of this acknowledge packet, such as at query operation 412 of FIG. 4, to determine whether to re-send the data packet to the repeater 610.

As discussed in relation to FIG. 7, the transport operations 710 and 716 operate according to different configurations of the two transport layers in use by the repeater 610 so that the transport layer connections are optimized, one for wired transfer and one for wireless transfer. These bridging operations of FIG. 7 for the repeater 610 thereby facilitate the transfer of data packets between the data network 612 and the pulse generator 604.

While the invention has been particularly shown and described with reference to illustrative embodiments thereof, it will be understood by those skilled in the art that various other changes in the form and details may be made therein without departing from the spirit and scope of the invention.

What is claimed is:

1. A method comprising:
    at an implantable pulse generator device for providing cardiovascular therapy to a patient, executing at least one application program that provides data that is to be exchanged from the implantable pulse generator to an external device and executing a set of information exchange instructions on the data obtained from the application program to:
        divide the data into packets, and
        apply header data to each packet that provides transport control information that controls the reconstruction of the application data from the data packets;
    wirelessly transmitting from the implantable pulse generator device each of the packets having the header data;
    receiving the packets at the external device; and
    analyzing the transport control information of the header data of each received packet to reorder the data received in the packets, when the data in the packets is received out of sequence, to reconstruct the application data.

2. The method of claim 1, wherein the transport control information corresponds to a Transport Control Protocol (TCP) protocol.

3. The method of claim 1, wherein the transport control information corresponds to a User Datagram Protocol (UDP) protocol.

4. The method of claim 1, wherein the transport control information corresponds to a TCP for transactions (T/TCP) protocol.

5. The method of claim 1, wherein the set of information exchange instructions are further executed on the data obtained from the application program to:
    apply header data to each packet that provides network routing information for each packet that specifies the intended receiving address for each packet.

6. The method of claim 5, further comprising:
    receiving each of the packets at a device external to the patient; and
    analyzing the network routing information of the header data of each received packet to determine where to route each of the packets for further transmission.

7. The method of claim 5, wherein the network routing information corresponds to the IPv4 protocol.

8. The method of claim 5, wherein the network routing information corresponds to the IPv6 protocol.

9. The method of claim 5, wherein the header data providing network routing information specifies a packet priority such that packets having a higher priority are wirelessly transmitted prior to packets with a lesser priority.

10. The method of claim 9, wherein the network routing information is IP and wherein the packet prioritization is specified in the precedence field.

11. The method of claim 5, further comprising:
    at the implantable pulse generator device, executing the information exchange instructions to:
        receive incoming data packets;
        extract header data to obtain network routing information to detect that the data packet is addressed to the implantable pulse generator device; and
        extract header data to obtain transport control information to determine how to reconstruct the data packets into data for the at least one application program.

12. The method of claim 1, wherein wirelessly transmitting each of the packets comprises transmitting each of the packets via an inductive coupling.

13. The method of claim 1, wherein wirelessly transmitting each of the packets comprises transmitting each of the packets via radio frequency.

14. The method of claim 1, including arbitrating to gain access to a physical link between the implantable device and the external device.

15. The method of claim 1, wherein analyzing the transport control information includes determining a socket for each packet when multiple sockets are established between the implantable pulse generator and the external device.

16. An implantable pulse generator device for providing cardiovascular therapy to a patient, comprising:
    at least one processing device configured to execute at least one application program to control the generation of electrical stimulation to provide the cardiovascular therapy and to utilize application data received from an external device, the at least one processing device being further configured to execute a set of information exchange instructions to:
        obtain incoming data packets, and
        extract header data that provides transport control information from each of the incoming data packets to allow the application data to be reconstructed from the packets for use by the at least one application program, the reconstruction including analyzing the transport control information of the header data of each received packet to reorder the data received in the packets, when the data in the packets is received out of sequence, to reconstruct the application data;
    a pulse generator in communication with the at least one processing device to generate electrical stimulation to provide the cardiovascular therapy; and
    a receiver in communication with the at least one processing device to wirelessly receive the incoming data packets having the transport control information and provide the incoming data packets to the at least one processing device.

17. The implantable pulse generator device of claim 16, wherein the transport control information corresponds to a TCP protocol.

18. The implantable pulse generator device of claim 16, wherein the transport control information corresponds to a UDP protocol.

19. The implantable pulse generator device of claim 16, wherein the transport control information corresponds to a TCP for transactions protocol.

20. The implantable pulse generator device of claim 16, wherein the at least one processing device is further configured to extract header data that provides network routing information from each of the incoming data packets to determine that the incoming data packets are addressed to the implantable pulse generator device.

21. The implantable pulse generator device of claim 20, wherein the network routing information corresponds to the IPv4 protocol.

22. The implantable pulse generator device of claim 20, wherein the network routing information corresponds to the IPv6 protocol.

23. The implantable pulse generator device of claim 20, wherein the at least one processing device is further configured to execute the at least one application program to produce data to be exchanged, and wherein the processing device is further configured to execute the set of information exchange instructions to:

divide the data from the at least one application program into outgoing packets,  provide header data for each packet that provides transport control information to allow the data to be reconstructed from the outgoing packets, and  provide header data for each packet that provides network routing information that specifies the intended receiving address for each data packet.

24. The implantable pulse generator of claim 16, wherein wirelessly receiving each of the packets comprises receiving each of the packets via an inductive coupling.

25. The method of claim 16, wherein wirelessly receiving each of the packets comprises receiving each of the packets via radio frequency.

26. An implantable pulse generator device, comprising:

processing means for executing an application program and for executing information exchange means, wherein the information exchange means is for sending and receiving data packets with an external device and exchanging application data of the data packets with the application program, wherein the information exchange means comprises:

means for dividing outgoing data from the application program into outgoing packets and for reconstructing incoming application data from incoming data packets, and   means for adding transport control information to outgoing data packets and for extracting transport control information from incoming data packets, the transport control information permitting reordering of the application data received in the packets, when the application data in the packets is received out of sequence, to reconstruct the application data; and  means for providing electrical stimulation.

27. The implantable pulse generator device of claim 26, wherein the transport control information corresponds to the TCP protocol.

28. The implantable pulse generator device of claim 26, wherein the transport control information corresponds to the UDP protocol.

29. The implantable pulse generator device of claim 26, wherein the transport control information corresponds to the TCP for transactions protocol.

30. The implantable pulse generator device of claim 26, further comprising:

means for adding network routing information to outgoing data packets and for extracting network routing information from incoming data packets.

31. The implantable pulse generator device of claim 30, wherein the network routing information corresponds to the IPv4 protocol.

32. The implantable pulse generator device of claim 30, wherein the network routing information corresponds to the IPv6 protocol.

33. The implantable pulse generator device of claim 26, further comprising means for wirelessly transmitting and receiving the packets.

34. A method of transferring data between a data network and an implantable pulse generator utilizing transport layer connections to transfer data in packets wherein the data network has a wired connection to a repeater in proximity to the implantable pulse generator and wherein the repeater has a wireless connection to the implantable pulse generator, the method comprising:

establishing a first transport layer connection between the data network and the repeater over the wired connection;

establishing a different second transport layer connection between the repeater and the implantable pulse generator over the wireless connection;

transferring a first data packet with first transport control header information from the data network to the repeater over the first transport layer connection; and  transferring the first data packet with second transport control header information from the repeater to the implantable pulse generator over the second transport layer connection, wherein the first and second transport control header information includes information as to how application data may be reconstructed from the data packets and to reorder the data received in the packets to reconstruct the application data when the data in the packets is received out of sequence.

35. The method of claim 34, further comprising:

transferring a second data packet from the implantable pulse generator to the repeater over the second transport layer connection; and  transferring the second data packet from the repeater to the data network over the first transport layer connection.

36. The method of claim 34, wherein the first and second transport layer connections are TCP connections, and wherein the second transport layer connection has a shorter re-transmission timeout than the first transport layer connection.

37. The method of claim 34, further comprising establishing a first network layer connection over the wired connection between the data network and the repeater to support the first transport layer connection and establishing a first network layer connection over the wireless connection between the repeater and the implantable pulse generator to support the second transport layer connection.

38. A system for transferring health care data, comprising:

a data network;

an implantable pulse generator; and a repeater located in proximity to the implantable pulse generator, wherein the repeater has a wired connection to the data network and a wireless connection to the implantable pulse generator, and wherein a first transport layer connection is established between the repeater and the data network and a different second transport layer connection is established between the repeater and the implantable pulse generator such that data packets traverse both the first transport layer connection and the second transport layer connection when passing between the data network and the implantable pulse generator, wherein a transport layer connection uses a transport layer protocol, and wherein data packets sent from the implantable pulse generator include transport control information in a header of each data packet, wherein the transport control information includes information as to how application data may be reconstructed by an endpoint on the data network and as to reordering of the data received in the packets to reconstruct the application data when the data in the packets is received out of sequence at the endpoint.

39. The system of claim 38, wherein the first transport layer connection has a longer re-transmission timeout than the second transport layer connection.

40. The system of claim 38, wherein the first transport layer connection and the second transport layer connection are TCP.

\* \* \* \* \*